(12) United States Patent
Cardamone et al.

(10) Patent No.: US 8,747,823 B2
(45) Date of Patent: Jun. 10, 2014

(54) COMPOSITIONS AND METHODS FOR TREATING A KERATIN BASED SUBSTRATE

(75) Inventors: Jeanette M. Cardamone, Lafayette Hill, PA (US); Paquita Erazo-Majewicz, Landenberg, PA (US); Nabil Naouli, Wilmington, DE (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/571,619

(22) Filed: Aug. 10, 2012

(65) Prior Publication Data

US 2014/0044664 A1    Feb. 13, 2014

(51) Int. Cl.
*A61Q 5/02*    (2006.01)
*A61Q 5/12*    (2006.01)

(52) U.S. Cl.
USPC .................. 424/70.14; 424/47; 424/70.27

(58) Field of Classification Search
None
See application file for complete search history.

(56) References Cited

U.S. PATENT DOCUMENTS

| | | | |
|---|---|---|---|
| 4,895,722 A | 1/1990 | Abe et al. | |
| 5,358,935 A | 10/1994 | Smith et al. | |
| 7,148,327 B2 | 12/2006 | Kelly et al. | |
| 2005/0124797 A1 | 6/2005 | Kelly et al. | |
| 2006/0165635 A1 | 7/2006 | Kelly et al. | |
| 2007/0237736 A1 | 10/2007 | Burgo et al. | |
| 2009/0165812 A1 | 7/2009 | Resnick et al. | |

FOREIGN PATENT DOCUMENTS

WO    WO 2004/047774    *    6/2004

OTHER PUBLICATIONS

Barba, C. et al., Restoring Important Hair Properties with Wool Keratin Proteins and Peptides, Fibers and Polymers, 2010, pp. 1055-1061, vol. 11 (7).
Roddick-Lanzilotta, A. et al., New Keratin Isolates: Actives for Natural Hair Protection, J. Cosmet. Sci., 2007, pp. 405-411, vol. 58.

* cited by examiner

*Primary Examiner* — Jyothsna Venkat
(74) *Attorney, Agent, or Firm* — John D. Fado; G. Byron Stover

(57) ABSTRACT

A composition containing sulfonated keratin with molecular weight distribution of about 96.8% 100 kDa to 100 Da and about 3.2% 250 kDa to 100 kDa, at least one cationic surfactant, and optionally an aqueous carrier. Generally the keratin is produced by a method involving treating wool with about 0.5 to about 1.0N NaOH in a bath volume:wool weight of about 5:1 to about 10:1 at about 40° C. to about 65° C. for about 4 to about 8 hours with dosing about every 1 to 3 hours with about 1% to about 10% by weight of bath of hydrogen peroxide. Also a method for treating a keratin based substrate involving contacting or applying the substrate (e.g., hair) with the composition.

10 Claims, 6 Drawing Sheets
(1 of 6 Drawing Sheet(s) Filed in Color)

COMPOSITIONS AND METHODS FOR TREATING A KERATIN BASED SUBSTRATE

BACKGROUND OF THE INVENTION

Disclosed is a composition containing sulfonated keratin with molecular weight distribution of about 96.8% 100 kDa to 100 Da and about 3.2% 250 kDa to 100 kDa, at least one cationic surfactant, and optionally an aqueous carrier. Generally the sulfonated keratin is produced by a method involving treating wool with about 0.5 to about 1N NaOH in a bath volume:wool weight of about 5:1 to about 10:1 at about 40° C. to about 65° C. for about 4 to about 8 hours with dosing about every 1 to 3 hours with about 1% to about 10% by weight of bath of hydrogen peroxide. Also disclosed is a method for treating a keratin based substrate (e.g., hair) involving contacting or applying the substrate with the composition.

The surface of human hair is damaged by combing, washing, and brushing, culminating in "split ends" where the inner cortical layer is exposed. The damage to human hair through environmental exposure, mechanical stress and abrasion, and chemical processing can be alleviated in part by conditioning treatments to correct for the problems of split ends, roughness, and dullness. Conditioners are used to improve wet and dry compatibility as a separate treatment for imparting softness and suppleness and preventing dryness and static flyaway in hair combing. After conditioning, hair is left with an aesthetically improved appearance but with little or no restoration of strength. Loss of 58% hair protein of 48 kDa and 60 kDa was reported after permanent waving (Han, Mi-Ok, et al., J. Cosmet. Sci., 59 (3): 203-215 (2008). Aminofunctional silicone emulsions were particularly effective in conditioning damaged hair to provide effective protection from damage associated with bleaching and oxidative dyeing (Berthiaume, M. D., et al., J. Soc. Of Cosmetic Chemists, 46(5), September/October 1995). High-viscosity, high amine content silicone microemulsions (e.g., dimethicones, cyclomethicones, amodimethicones, and trimethylamodimethicones) have been found to provide significant conditioning properties to damaged hair, restore shine and smoothness, and ease of combing in correcting for fly-away hair and wet and dry combing performance. However, silicone additives are known to build up and cause dullness and a greasy-appearance.

We have found that sulfonated keratin with molecular weight distribution of about 96.8% 100 kDa to 100 Da and about 3.2% 250 kDa to 100 kDa can replace silicone in formulated conditioners to provide the desired beneficial effects.

SUMMARY OF THE INVENTION

Disclosed is a composition containing sulfonated keratin with molecular weight distribution of about 96.8% 100 kDa to 100 Da and about 3.2% 250 kDa to 100 kDa, at least one cationic surfactant, and optionally an aqueous carrier. Generally the keratin is produced by a method involving treating wool with about 0.5 to about 1.0N NaOH in a bath volume:wool weight of about 5:1 to about 10:1 at about 40° C. to about 65° C. for about 4 to about 8 hours with dosing about every 1 to 3 hours with about 1% to about 10% by weight of bath of hydrogen peroxide. Also disclosed is a method for treating a keratin based substrate involving contacting or applying the substrate with the composition.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
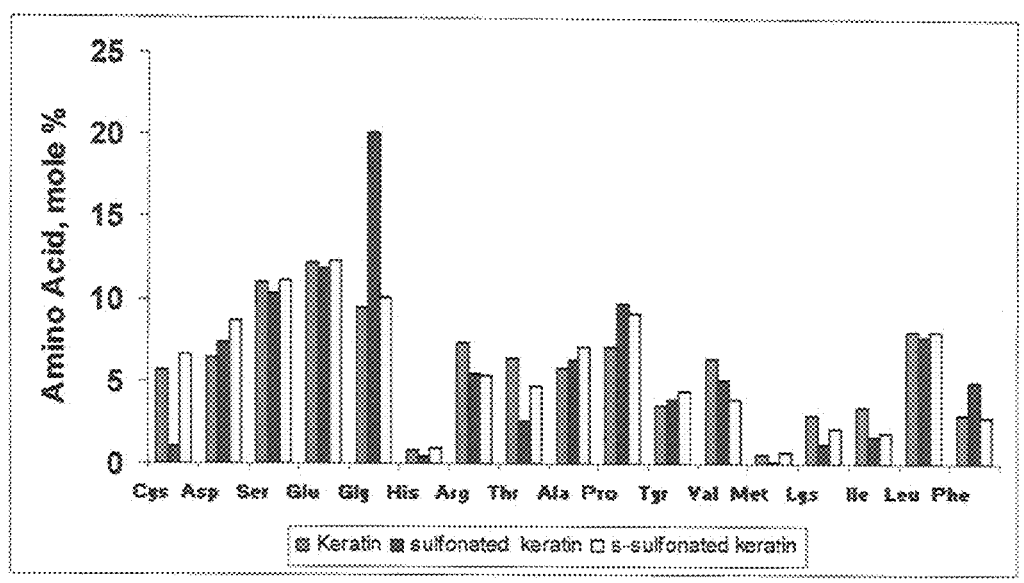
FIG. 1 shows amino acid content of our sulfonated keratin and commercial S-sulfonated keratin as described below.

Disclosed is a composition containing sulfonated keratin with molecular weight distribution of about 96.8% (e.g., 96.8%) 100 kDa to 100 Da and about 3.2% (e.g., 3.2%) 250 kDa to 100 kDa, at least one cationic surfactant, and optionally an aqueous carrier. Generally the keratin is produced by a method involving treating wool with about 0.5 to about 1N NaOH (e.g., 0.5 to 1N; preferably about 1N (e.g., 1N)) in a bath volume:wool weight of about 5:1 to about 10:1 (e.g., 5:1 to 10:1; preferably about 7:1 (e.g., 7:1)) at about 40° C. to about 65° C. (e.g., 40° C. to 65° C.; preferably about 60° C. (e.g., 60° C.)) for about 4 to about 8 hours (e.g., 4 to 8 hours; preferably about 6 hours (e.g., 6 hours)) with dosing about every 1 to 3 hours (e.g., 1 to 3 hours; preferably about 2 hours (e.g., 2 hours)) with about 1% to about 10% (e.g., 1% to 10%; preferably about 5% (e.g., 5%)) by weight of bath of hydrogen peroxide within the pH range of about 12 to about 13 (e.g., 12-13). Also disclosed is a method for treating a keratin based substrate involving contacting or applying the substrate with the composition.

Our unique hydrolysis method was applied to wool fiber to extract keratin protein. When our keratin in powder form was incorporated into a conditioner the keratin constituent imparted strength to the hair. Our hydrolysis method does not utilize the procedure described in U.S. Pat. No. 7,148,327 or in J. Cosmet. Sci., 58: 405-411 (2007) involving isolating keratin by using oxidative sulfitolysis with sodium sulfite or sodium metabisulfite and the oxidant cuprammonium hydroxide with the subsequent use of alkaline solution of 50% hydrogen peroxide to completely dissolve any remaining wool.

Human hair is the focus of attention for the so-called Brazilian treatments that are considered innovative for permanently straightening the hair. However, this treatment has the disadvantage of weakening the hair. Our unique keratin was found to strengthen hair and, when incorporated into a hair conditioner, rebuilds strength into damaged hair.

Our keratin, in the forms of gel, salve, or emollient, can be applied as stand-alone products or in formulations to clean and/or condition keratin based substrates, such as hair, skin, and nails.

The cationic surfactant in the composition includes, for example, amidoamine cationic surfactants such as those derived from stearamidopropyl dimethylamine (N-(3-dimethylaminopropyl)octadecanamide).

Our sulfonated keratin, formed from the oxidation hydrolysis of wool, was recovered as functional peptides and protein homologs. When incorporated into a commercial conditioner which contained an amidoamine cationic surfactant, the keratin led to permeation of the conditioner into hair. Without being bound by theory, the ability to permeate the hair for beneficial effects was attributed to the ionic attraction of anionic damaged hair with cationic keratin-surfactant complex where the combination of anionic keratin with cationic surfactant was regulated to provide overall cationic charge for affinity to the damaged hair. Sulfoxides bear Sulfoxides bear three favorable properties (i.e., good solubility, good hydrating power, and penetration into keratinic substances) thus making these hydration agents superior to those already known in the state of the art; the adhesion of our keratin adduct to keratinous damaged hair provided the strengthening effect observed.

Our keratin, fully oxidized with sulfonate sulfoxide (—$SO_3^-$) content in FIG. 1, was extracted from wool with the preserved microfibrillar structure of intermediate filaments, chemical structure, molecular weight, and preserved amino acid content of native keratin in low MW peptide and high MW protein forms. As (—$SO_3^-$) functional protein, it was effective in combining with an amidoamine cationic surfactant derived from stearamidopropyl dimethylamine (N-(3-dimethylaminopropyl)octadecanamide) commonly used in conditioner formulations, for example in TRESemmé (formulation 5 in Table 2). The substantive combination of ionic nature of our keratin —$SO_3^-$ was the product of vigorous alkaline peroxide oxidation of —SH thiols giving keratin sulfonate products. Severe oxidation proceeds to form disulfide, thiosulfinate, thiosulfonate, disulfide trioxide, disulfide tetraoxide, and finally (with hydrolysis) sulfonic acid.

Reaction pathway for complete oxidation hydrolysis of keratin (R):

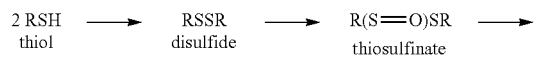

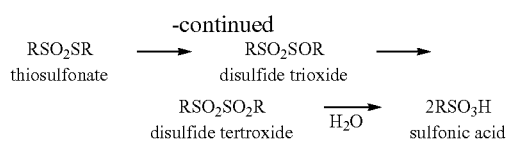

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Our method generally followed the procedure of applying 0.5 to 1.0N NaOH, optimally 1N NaOH, in a liquor ratio (bath volume:wool weight) of 5:1 to 10:1, optimally 7:1, at 40° C. to 65° C., optimally 60° C. for 4 to 8 hours, optimally 6 hours, with dosing every 1 to 3 hours, preferably 2 hours with 1% to 10% (by weight of bath), preferably 5% of 50% hydrogen peroxide, for complete solubility of the wool fiber. To extract keratin from wool in the form of hydrolysate, typically 125 grams of wool was contacted with a 1L solution which was constituted to pH 12-13 with 40 grams sodium hydroxide. After three hours of incubation with stirring at 60° C., to this solution was added 12.5 mL of 50% hydrogen peroxide. The hydrolysis reaction ensured at 60° C. for from 4 to 6 hours from initial processing time, to obtain completely solubilized wool in the form of keratin hydrolysate solution. The solution was the subject-raw-material for treating a keratin based substrate.

Keratin hydrolysate, amber in appearance, was filtered to remove particulate matter. It was left undialyzed to contain low MW sulfur salts and fractions of low MW keratin peptides <100 Da and high MW proteins up to 250 kDa. The method of oxidizing —SH group into sulfonic acid group followed the following scheme:

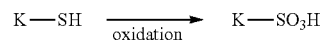

Human hair is naturally strong and its strength is due mainly to its structure. A virgin Caucasian single fiber hair can support 100 g before breakage. We determined the effects of applying keratin proteins extracted from wool on the mechanical properties of bleached hair. Various conditioners were formulated containing wool keratin to treat bleached hair. Sixty single hair fibers were taken from each conditioner-treated tress and the cross sectional area was measured and the fibers were extended to the break point at a rate of 12.5 mm/min. A comparison between the control and treatment groups was carried out using a "t" test with a p value of less than 0.05. Analysis of the break strain and stress for each hair tress demonstrated that wool keratin incorporated into conditioners imparted strength to hair and our keratin surprisingly provided the highest beneficial effect for strengthening bleached hair.

The tensile properties of hair were measured at high humidity to evaluate the degree of covalent damage/repair due to product treatment. All hair fibers used in the experiment were measured for cross sectional area before tensile testing to enable normalization of the load parameters.

Conditioner Formulation: Three keratin-containing conditioners, including a negative control which contained no keratin #1, were formulated as #2, #3, and #4 (Table 1).

Hair Strands Treatment: All experiments were performed using bleached European hair (from International Hair Importers, New York). The hair tresses were bleached for 90 minutes followed by intensive rinsing when received. In hair tresses, prewashed tresses were wetted under running water at 35°-40° C. with a controlled flow rate set at 4 L/min. Each tress was washed twice with sodium lauryl sulfate, SLES (2EO), using 0.1 g surfactant/gram tress, washing twice (30 seconds each time) then air dried overnight at 73° F. and 50% relative humidity. Each twice washed tress was hand combed 5 times with large teeth comb and 5 times with small teeth comb (10 times total).

Hair Sample Treatments: Each bleached hair tresses (3 g) was treated with 0.6 g conditioner (formulations 1-4) once for 30 seconds and dried overnight at 73° F. and 50% relative humidity. The dried tresses were labeled tress 1-4, which corresponded to the type of treatment formulation. For example, bleached hair tress 1 was treated with conditioner formulation number 1, therefore it was labeled tress number 1. For the commercial control, the bleached hair tress was washed with Tresemme shampoo 0.3 (g) twice, then with 0.6 (g) Tresemme Anti-Breakage conditioner once and labeled tress number 5.

Measurement of cross sectional area: 60 single fibers were taken from each tress and permanently mounted in PVC lined brass crimps. The cross sectional area of each fiber was measured using the Fiber Dimensional Analysis System (FDAS765), which incorporated the Mitutoyo laser scanner (Dia-Stron Limited, Andover, UK). The FDAS recorded multiple diameter measurements from the fiber and calculated a cross sectional area based on an ellipse. The laser micrometer accuracy was better than 0.1 microns.

Measurement of tensile properties: The mounted hair fibers were loaded into the MTT675 cassette and then equilibrated at 85% relative humidity overnight. The fibers were then extended to break at 12.5 mm/min (40% strain rate/min) using the MTT675 automated tensile tester (Dia-Stron Limited, Andover. UK) at 72° F. and 85% relative humidity.

The mechanical properties of bleached hair after the application of the keratin formulations were compared to the mechanical properties of bleached hair treated with TRESemmé, formulation 5, shampoo-conditioner system containing hydrolyzed keratin as shown in the label of the commercial product. The student "t" test was applied to determine statistical significance as a p value of less than 0.05. See Table 2.

Conclusion: After mechanical testing, the hair tress sample number 1, designated as the control, and the series of keratin conditioners were compared for statistical differences using the "t" test for significance. A "p" value of less than was 0.05 was taken as statistically significant. Of the tresses series (1-5), none of the treatments modified the cross sectional area, Young's Modulus, or the yield parameters at either 15% or 25% strain values. All formulations incorporating keratin showed a positive effect for hair strengthening; however our keratin surprisingly proved most beneficial for imparting strength to bleached hair. Our keratin in conditioning formulation number 2 gave an increase in both break strain (4%) and break stress (8%), and although these values were not large they were statistically significant at p<0.05 and <0.01 respectively.

Our keratin with sulfoxide functionality strengthened hair and was different from commercial keratin with S-sulfo functionality which is used to treat damaged hair. Sulfur-rich keratin treated with alkali formed lanthionine by elimination of one of the sulphur atoms of the dithio bond of the cystine residues with the formation of a thioether (lanthionine) linkage (-(alanin-3-yl)-L-cysteine, with the chemical formula (HOOC—CH(NH$_2$)—CH$_2$—S—CH$_2$—CH(NH$_2$)—COOH). Lanthionine, a monosulfide (thioether) analog of cystine, is composed of two alanine residues that are crosslinked on their β-carbon atoms by a thioether linkage with the elimination of one of the sulphur atoms of the dithio bond of the cystine residues, whereby a new thioether amino acid is formed. The complete oxidation of cystine to cysteic acid proceeded through the following steps: Cystine, HOOCCH(NH$_2$)CH$_2$SSCH$_2$CH(NH$_2$)COOH, was converted to lanthionine by alkaline hydrolysis and subsequently to the oxidized forms of lanthionine sulfoxide HOOCCH(NH$_2$)CH$_2$S(O)CH$_2$CH(NH$_2$)COOH, lanthionine sulfone HOOCCH(NH$_2$)CH$_2$S(O$_2$)CH$_2$CH(NH$_2$)COOH, and cysteic acid HOOCCH(NH$_2$)CH$_2$SO$_3$H, by dosing with hydrogen peroxide.

Our keratin was formed by vigorous oxidation of —SH thiols which gave sulfonic acids (RSO$_3$H) as the products. This oxidation was accomplished in steps to give disulfide, thiosulfinate, thiosulfonate, disulfide trioxide, disulfide tetraoxide, and finally (with hydrolysis) sulfonic acid:

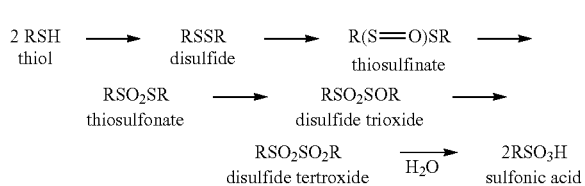

In our system we dosed with alkaline peroxide because we did not use a stabilizer to control the peroxide decomposition. Alkaline hydrogen peroxide was notable for a particularly strong oxidizing action and the substrate, keratin with sulfoxide groups, is hydrophilic. The action of alkali on wool was to transform cystine to lanthionine. Cysteic acid was formed on the treatment of wool with alkali, the amount formed depending on the intensity of treatment. Without being bound by theory, oxidation was postulated by nuceophilic attack on one of the sulfur atoms of the disulfide links, depending on the electronic charge of the groups near to this link. Hydrogen peroxide oxidized the cystine in wool partly to cysteic acid and partly to cystine disulfoxide.

Commercial keratin (Keratec™ Limited, New Zealand and Keraplast Technologies, LLC, San Antonio, Tex.) was chemically different from our keratin; the commercial keratin proceeded through the reduction of the disulfide bond to form keratin in the S-sulfonated form:

which supposedly reformed —S—S— bonds in damaged hair. The S-sulfonate ($CySSO_3$) formed by oxidation sulfitolysis with a sulfonating agent formed cysteine, —SH, and S-sulfocysteine, and —$SO_3^-$ which forms ($SCH_2CH(NH_2)$ $CO_2H)_2$, a dimeric amino acid by oxidation of two cysteine residues that covalently linked to make a disulfide bond. In hand-cream, S-sulfonated keratin exhibited water-holding capacity, hydration, and elasticity. S-sulfonated and thiol proteins treated with sodium hydroxide and peroxide reform disulfide bonds to form crosslinked keratin networks.

Commercial hydrolyzed keratin products, Keratec Pep™ (Keratec Products, distributed by Croda Chemicals Europe Personal care, East Yorkshire, England), are amber hydrolysate solutions used for personal care applications. They supposedly contain cystine content of ~4% of which the highest proportion (~65%) is present as S-sulfo cysteine or Bunte Salt, —S—$SO_3^-$ form, for beneficial effects of softening and conditioning hair fibers. Conditioning supposedly proceeds through Bunte salt reduction and permanent attachment to reduced (damaged) hair as follows:
Reaction of Keratec pep with reduced hair (permed or damaged):

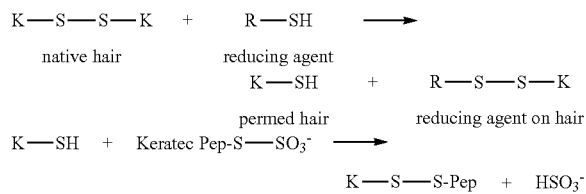

It is assumed that hair keratin can reform disulfide bonds in damaged hair and directly affect hair properties. In theory, on exposure to reducing conditions such as thioglycollate in perming, the reactive S-Sulfo groups are converted to cysteine (—SH) which are then capable of crosslinking with either themselves or keratin substrates such as hair to reform disulfide linkages (—S—S—). Reduced hair with cysteine groups supposedly can link to Keratec Pep for beneficial effects.

Characteristic and Distinct Differences. Our Sulfonated Keratin and Commercial S-sulfonated Keratin: Amino acid analysis with HPLC-Hydrolysis using 6N HCl to hydrolyze protein and peptide samples was employed to document amino acid content. The cysteine (Cys) amino acid content in mol % of total amino acids for our sulfonated keratin was low, consistent with the loss of cystine which indicated that lanthionine content was not appreciable. Relatively high cysteine content for commercial S-sulfonated keratin was consistent with formation of cysteine-S-sulfonate.

FTIR Spectroscopy-Formation of sulfoxides from the oxidation of keratin was followed by Fourier transform infra-red (FTIR) spectrometry. Commercial S-sulfonated keratin was formed by sulfitolysis oxidation of cystine residues to form cysteine-S-sulfonate. Under atmospheric conditions, or in the presence of an oxidant such as dilute $H_2O_2$, thiol functions can combine to form disulfide bonds and return the chemical nature of the keratin material to one much closer to the original form, that is, to proteins containing a high proportion of cystine disulfide links. With FTIR spectroscopy, the S-sulfonate group was detected by a strong, sharp absorbances at 1022 cm-1, at 1040 $cm^{-1}$ to 1048 $cm^{-1}$, and 1210 $cm^{-1}$ to 1215 $cm^{-1}$. The presence of these bands was diagnostic for the presence of S-sulfonate (Bunte Salt).

Our completely oxidized keratin was detected by sulfoxide IR absorptions for sulfonic acid (1041 $cm^{-1}$), sulfinic acid or monoxide (1073 $cm^{-1}$), disulfoxide (1111 $cm^{-1}$), thiosulfonate (1167 $cm^{-1}$), Cy-S—$SO_3^-$ (1012 $cm^{-1}$); cysteic acid, $CySO_3H$ (1045 $cm^{-1}$); cysteine-monoxide, Cy-SO—S-Cy (1073 $cm^{-1}$ to 1080 $cm^{-1}$), and cystine S-dioxide, and $CySO_2$—S-Cy (1137 $cm^{-1}$). Typical cysteic acid IR absorptions fall within the range of 1040 $cm^{-1}$ and 1175 $cm^{-1}$.

Figure 2A:
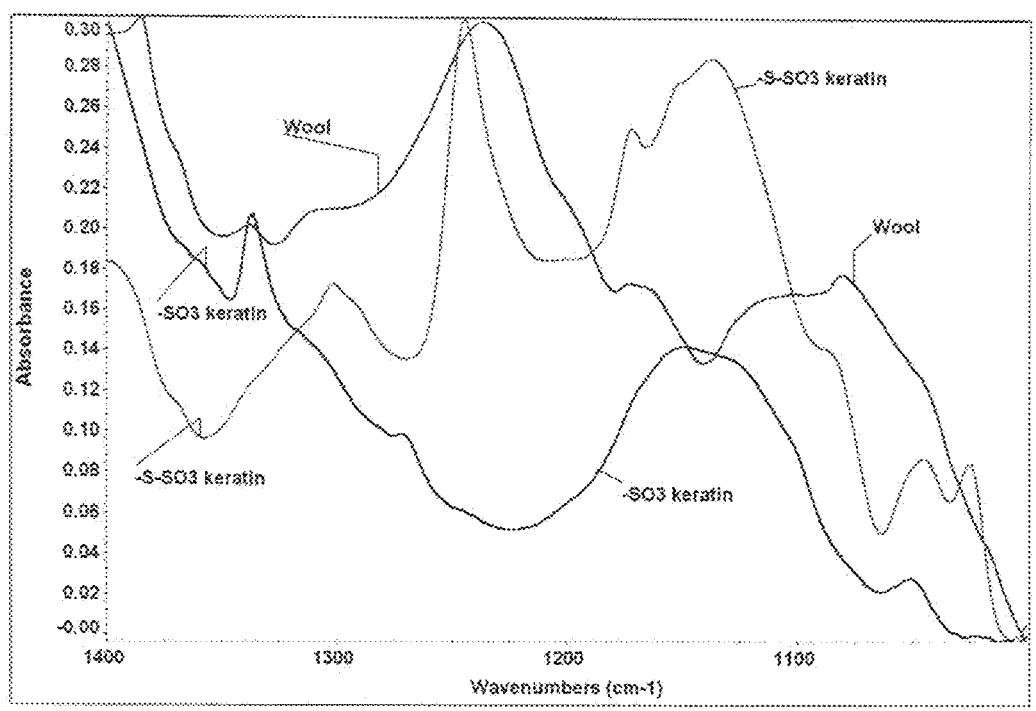
FIG. 2(a) shows composite FTIR spectra of unresolved absorption bands in the 1400 to 1000 $cm^{-1}$ region, descriptive of chemical differences among unaltered wool, our sulfonated keratin, —$SO_3$ keratin, and commercial S-sulfonated keratin, —S—$SO_3$ keratin, as described below.
Figure 2B:
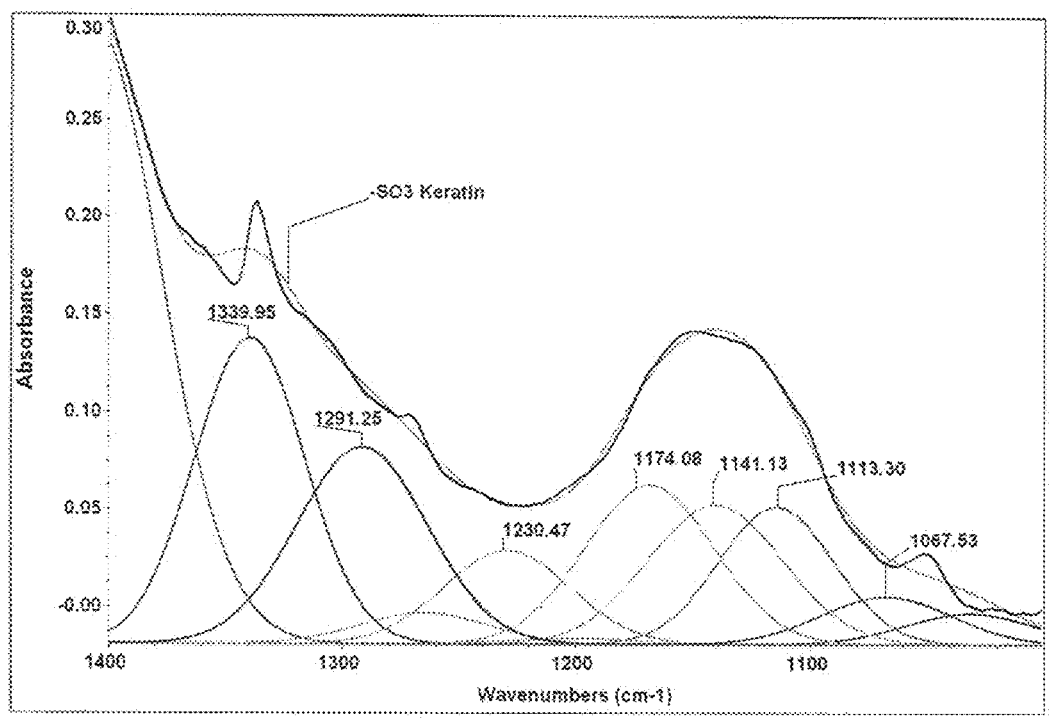
FIG. 2(b) shows peak-resolved FTIR spectra of individual absorption bands for our sulfonated —$SO_3$ keratin (cysteic acid, 1040 $cm^{-1}$) as described below.
Figure 2C:
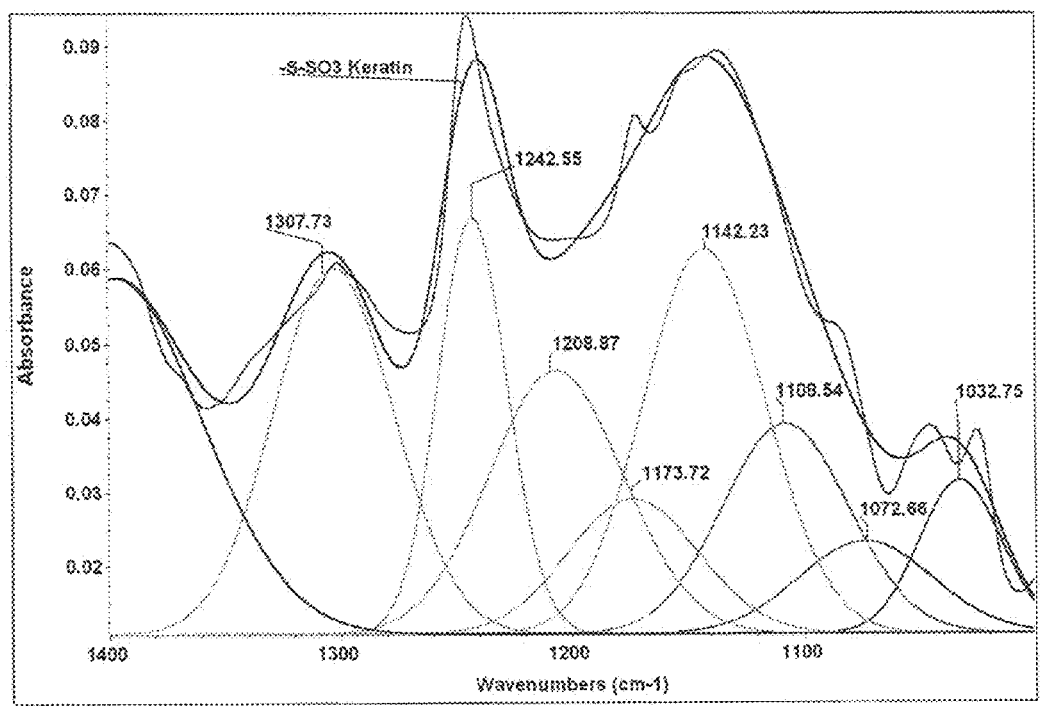
FIG. 2(c) shows peak-resolved FTIR spectra of individual absorption bands for S-sulfonated commercial keratin, —S—$SO_3$ keratin (cysteic acid, 1040 $cm^1$ as described below.
Figure 3:
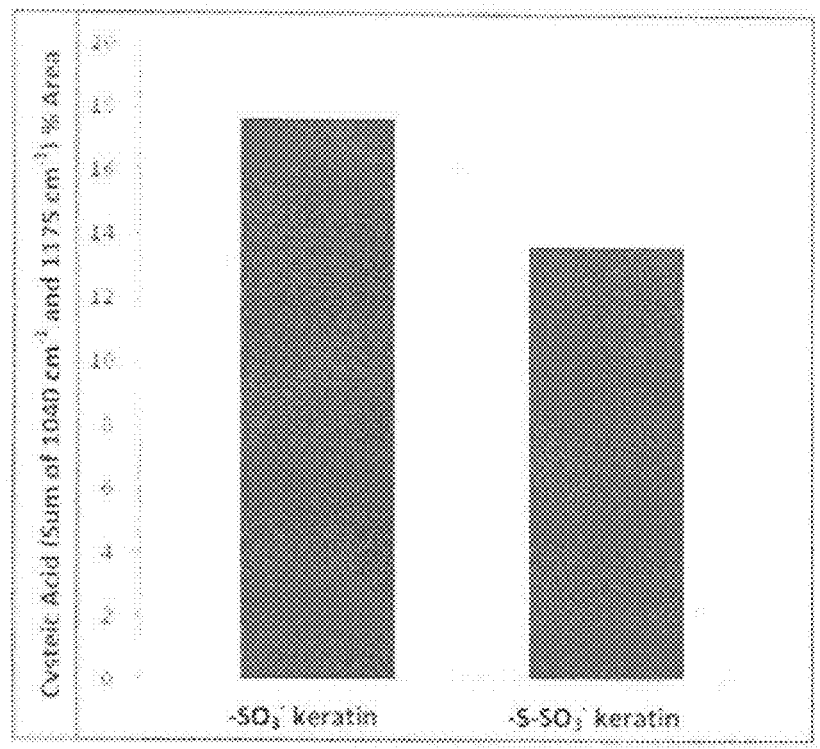
FIG. 3 shows the difference in cysteic acid content when our sulfonated keratin is compared to commercial S-sulfonated keratin as described below.
Figure 4:
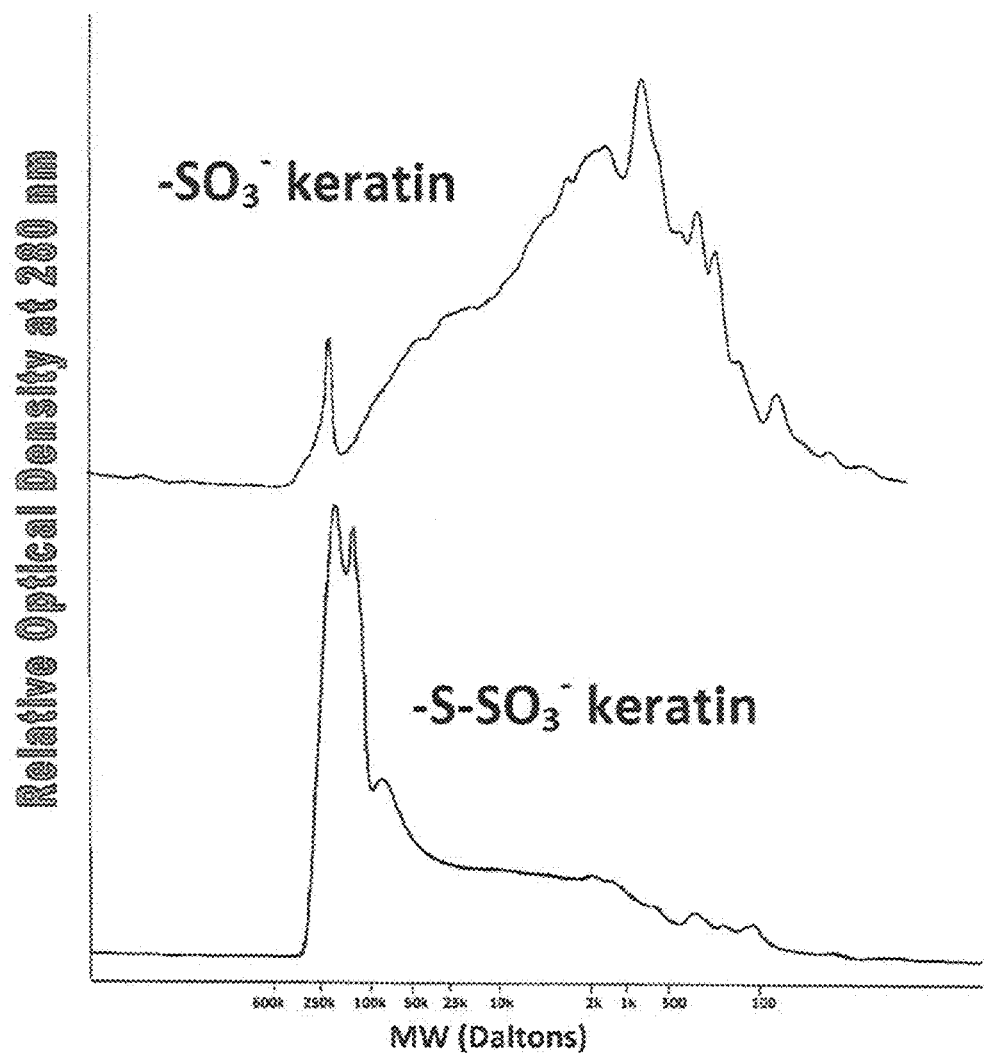
FIG. 4 shows molecular weight distributions of our sulfonated keratin and commercial S-sulfonated keratin as described below. Our keratin showed a high content and broad distribution of keratin from 250 kDa to 100 Da and lower content of narrow distribution of higher 250 kDa molecular weight protein. Commercial S-sulfonated keratin showed highest content of narrow distribution molecular weight protein of 250 kDa and lower content of the broad distribution of molecular weight fractions from 250 kDa to 100 Da.

Peak resolutions for these bands are shown in FIG. 2 (*b* and *c*) where the spectra show IR resolved peaks of our sulfonated keratin, and commercial S-sulfonated keratin. Note: cysteic acid, 1040 cm–1. FIG. 2(*a*) shows a composite FTIR spectra of native wool and chemically treated wool in the different forms: —SO3 keratin and —S—SO3 keratin. FIG. 3 shows a graph of IR analysis for cysteic acid content of our sulfonated keratin and commercial S-sulfonated keratin. Note: cysteic acid content was appreciably higher in our sulfonated keratin. FIG. 4 shows Size Exclusion Chromatography to detect differences in molecular weight distributions between our sulfonated keratin where there was a much higher density of broad molecular weight keratin of 100 Da to 250 kDa compared to commercial S-sulfonated keratin. Table 3 shows that our sulfonated keratin was 96.8% 100 kDa to 100 Da and 3.2% 250 kDa to 100 kDa whereas commercial S-sulfonated keratin was 61.8% 100 kDa to 100 Da and 38.7% 250 kDa to 100 kDa.

Conclusion: Clearly our sulfonated keratin was of different chemical composition than S-sulfonated commercial keratin. Our keratin contained a higher amount of broad MW fractions which were surprisingly found beneficial for strengthening hair when formulated in hair conditioners. After applying unformulated commercial S-sulfonated keratin this statistically beneficial effect had not been reported.

All of the references cited herein, including U.S. Patents, are incorporated by reference in their entirety. Also incorporated by reference in their entirety are the following references: Bailey, K., and Edsall, J. T. (Eds.), Academic Press, NY, p. 278, 1954; Barba, C., et al., Fibers and Polymers, 11(7): 1055-1061 (2010); Bellamy, L. J,. Infrared Spectra of Complex Molecules, 3rd Ed., Wiley, New York, pages 407-408 (1975); Berthiaume, M. D., et al., J. Soc. Of Cosmetic Chemists, 46(5), September/October 1995; Cardamone, J. M., and J. G. Phillips, Textile Research Journal, 77: 277-283 (2007); Cardamone, J. M., et al., Research Letters in Material Science, Vol. 2009, ID 147175, 2009; Cardamone, J. M., Journal of Molecular Structure, 969: 97-105 (2010); Han, Mi-Ok, et al., J. Cosmet. Sci., 59(3): 203-215 (2008); Harris, M., and A. L. Smith, Bur. Stand. J. Res., Wash., 16: 301 (1936); Holt, L. A., J. Soc. Cosmet. Chem., 42: 351-359 (1991); Horn, M. J., et al., Journal of Biological Chemistry, 138: 141-149 (1941); Kauder, O. S., Thiols in Encyclopedia of Chemical technology, Vol. 22, 3rd ed, Wiley-Interscience, NY, pages 946-963 (1983); Kelly, R. J., et al., U.S. Pat. No. 7,148,327; Kelly, R. J., et al., U.S. Patent Application Publication 2009/0069541; Kice, J. L., J. Org. Chem., 28(4): 957-961 (1963); Lipton, S. H., et al., J. Agric. Food Chem., 25 (3): pp 624-628 (1977); Matz, G. F., and R. LaMar, U.S. Pat. No. 6,110,451; Robbins, C. R., Chemical and Physical Behavior of Human Hair, Van Nostrand Reinhold, New York, pp. 29 and 70 (1979); Miro, P., et al., J. Soc. Dyers and Colourists, 9: 407-409 (1969); Roddick-Lanzilotta, A& R. Kelly, Protecting the Natural Hair with Keratin Biopolymers. Cosmetics and Toiletries, 121 (5), 2006; Roddick-Lanzilotta, A., et al., J. Cosmet. Sci., 58:405-411 (2007); Ward, W. H., and H. P.

Lundgren, in Advances in Protein Chemistry, Vol. IX, Anson, M. K. L., Galande, A. K., and A. F. Spatola, Letters in Peptide Science, 8: 247-251 (2002); Westlake, H. E., and G. Dougherty, J. AM Chem. Soc., 1942, 64(1): 149-150 (1942).

Thus, in view of the above, the present invention concerns (in part) the following:

A composition comprising (or consisting essentially of or consisting of) sulfonated keratin with molecular weight distribution of about 96.8% 100 kDa to 100 Da and about 3.2% 250 kDa to 100 kDa, at least one cationic surfactant, and optionally an aqueous carrier.

The above composition, wherein said cationic surfactant is an amidoamine cationic surfactant.

The above composition, wherein said cationic surfactant is an amidoamine cationic surfactant derived from stearamidopropyl dimethylamine (N-(3-dimethylaminopropyl)octadecanamide).

The above composition, wherein said sulfonated keratin is produced by a method comprising (or consisting essentially of or consisting of) treating wool with about 0.5 to about 1.0N NaOH in a bath volume:wool weight of about 5:1 to about 10:1 at about 40° C. to about 65° C. for about 4 to about 8 hours with dosing about every 1 to 3 hours with about 1% to about 10% by weight of bath of hydrogen peroxide.

A method for treating a keratin based substrate comprising (or consisting essentially of or consisting of) contacting or applying said substrate with the above composition.

The above method, comprising a step of spraying, dipping, washing, brushing or rubbing the keratin based substrate with the composition.

The above method, wherein the method does not have a rinsing step.

The above method, wherein the composition is a shampoo.

The above method, wherein the composition is a conditioner.

The above method, wherein the composition is a hair spray.

The above method, wherein said keratin based substrate is hair.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Hair Conditioning Formulations

| | Conditioner Formulation number | | | |
|---|---|---|---|---|
| | 1 negative control | 2 our keratin | 3 cationic keratin | 4 commercial keratin |
| Water | 96.17 | 93.67 | 93.67 | 93.67 |
| Lactic acid | 0.13 | 0.13 | 0.13 | 0.13 |
| Stearamidopropyl dimethylamine | 0.7 | 0.7 | 0.7 | 0.7 |
| Cetearyl alcohol | 2.5 | 2.5 | 2.5 | 2.5 |
| 2.5% keratin protein | — | 2.5 | 2.5 | 2.5 |
| Preservative | 0.5 | 0.5 | 0.5 | 0.5 |

TABLE 2

| Conditioners | Bleach Hair Tresses # | Break Extension % Strain | Break Load gmf, ×10$^{-1}$ | Break Stress gmf/sq micron, ×10$^{-2}$ | Work to Break Joules, ×10$^{-3}$ |
|---|---|---|---|---|---|
| Negative Control | 1 | 53.23 ± 5.58 | 6.15 ± 1.71 | 1.67 ± 2.45 | 5.54 ± 0.17 |
| our keratin | 2 | 55.51 ± 5.07 | 6.50 ± 1.37 | 1.81 ± 0.19 | 5.99 ± 0.14 |
| Cationic S-Sulfonated Keratin | 3 | 53.63 ± 5.35 | 6.40 ± 1.49 | 1.78 ± 0.16 | 5.68 ± 0.15 |
| Commercial S-Sulfonated keratin | 4 | 54.54 ± 5.91 | 6.45 ± 1.72 | 1.72 ± 0.19 | 5.89 ± 0.19 |
| TRESemmé shampoo & conditioner | 5 | 54.2 ± 4.21 | 6.27 ± 1.78 | 1.73 ± 0.16 | 5.63 ± 1.82 |

TABLE 3

Molecular weight distributions, %, from Size Exclusion Chromatography of soluble wool keratin

| | 250 kDa to 100 kDa Narrow area | 100 kDa to 100 Da Broad area |
|---|---|---|
| Our Sulfonated Keratin | 3.2 | 96.8 |
| Commercial S-sulfonated Keratin | 38.7 | 61.8 |

We claim:

1. A composition comprising sulfonated keratin with molecular weight distribution of about 96.8% 100 kDa to 100 Da and about 3.2% 250 kDa to 100 kDa, at least one cationic surfactant, and an aqueous carrier; wherein said cationic surfactant is an amidoamine cationic surfactant; wherein said sulfonated keratin is produced by a method comprising treating wool with about 0.5 to about 1.0N NaOH in a bath volume; wool weight of about 5:1 to about 10:1 at about 40° C. to about 65° C. for about 4 to about 8 hours with dosing about every 1 to 3 hours with about 1% to about 10% by weight of bath of hydrogen peroxide.

2. The composition according to claim 1, wherein said amidoamine cationic surfactant is derived stearamidopropyl dimethylamine (N-(3-dimethylaminopropyl)octadecanamide).

3. A method for treating a keratin based substrate comprising contacting or applying said substrate with the composition of claim 1.

4. The method according to claim 3, comprising a step of spraying, dipping, washing, brushing or rubbing the keratin based substrate with the composition.

5. The method according to claim 3, wherein the method does not have a rinsing step.

6. The method according to claim 3, wherein the composition is a shampoo.

7. The method according to claim 3, wherein the composition is a conditioner.

8. The method according to claim 3, wherein the composition is a hair spray.

9. The method according to claim 3, wherein said keratin based substrate is hair.

10. A composition consisting of sulfonated keratin with molecular weight distribution of about 96.8% 100 kDa to 100 Da and about 3.2% 250 kDa to 100 kDa, an amidoamine cationic surfactant, and an aqueous carrier.

\* \* \* \* \*